US009969788B2

(12) United States Patent
Lee

(10) Patent No.: US 9,969,788 B2
(45) Date of Patent: *May 15, 2018

(54) METHODS OF TREATING DAMAGED CARTILAGE TISSUE USING GROWTH FACTORS FUSED TO HEPARIN BINDING SEQUENCES

(71) Applicant: The Brigham and Women's Hospital, Inc., Boston, MA (US)

(72) Inventor: Richard Lee, Weston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/877,474

(22) Filed: Oct. 7, 2015

(65) Prior Publication Data

US 2016/0024170 A1 Jan. 28, 2016

Related U.S. Application Data

(63) Continuation of application No. 11/979,708, filed on Nov. 7, 2007, now Pat. No. 9,187,517.

(60) Provisional application No. 60/858,406, filed on Nov. 13, 2006.

(51) Int. Cl.

| | | |
|---|---|---|
| *A61K 38/30* | (2006.01) | |
| *C07K 14/65* | (2006.01) | |
| *C07H 21/04* | (2006.01) | |
| *C07K 14/475* | (2006.01) | |
| *C07K 14/49* | (2006.01) | |
| *C12N 15/62* | (2006.01) | |
| *A61K 35/30* | (2015.01) | |
| *A61K 35/32* | (2015.01) | |
| *A61K 35/34* | (2015.01) | |
| *C07K 14/47* | (2006.01) | |
| *C12N 5/0793* | (2010.01) | |
| *C12N 5/077* | (2010.01) | |
| *A61K 38/00* | (2006.01) | |

(52) U.S. Cl.
CPC .............. *C07K 14/65* (2013.01); *A61K 35/30* (2013.01); *A61K 35/32* (2013.01); *A61K 35/34* (2013.01); *C07H 21/04* (2013.01); *C07K 14/47* (2013.01); *C07K 14/475* (2013.01); *C07K 14/49* (2013.01); *C12N 5/0619* (2013.01); *C12N 5/0655* (2013.01); *C12N 5/0657* (2013.01); *C12N 15/62* (2013.01); *A61K 38/00* (2013.01); *C07K 2319/035* (2013.01); *C07K 2319/33* (2013.01); *C12N 2501/105* (2013.01)

(58) Field of Classification Search
None
See application file for complete search history.

(56) References Cited

U.S. PATENT DOCUMENTS

| | | | |
|---|---|---|---|
| 5,670,483 | A | 9/1997 | Zhang et al. |
| 5,786,217 | A | 7/1998 | Tubo et al. |
| 6,037,329 | A | 3/2000 | Baird et al. |
| 6,150,163 | A | 11/2000 | McPherson et al. |
| 6,548,630 | B1 | 4/2003 | Zhang et al. |
| 7,399,831 | B2 | 7/2008 | Lee et al. |
| 7,429,567 | B2 | 9/2008 | Lee et al. |
| 9,187,517 | B2 * | 11/2015 | Lee .................. C07H 21/04 |
| 2004/0063619 | A1 * | 4/2004 | Carson ............ A61K 38/1709 514/23 |
| 2004/0087505 | A1 | 5/2004 | Pena et al. |
| 2005/0222394 | A1 | 10/2005 | Zamora et al. |
| 2006/0088510 | A1 | 4/2006 | Lee et al. |
| 2006/0148703 | A1 | 7/2006 | Lee et al. |
| 2006/0172931 | A1 | 8/2006 | San Antonio et al. |
| 2008/0227696 | A1 * | 9/2008 | Takahashi ............ C07K 14/49 514/1.1 |

FOREIGN PATENT DOCUMENTS

| | | |
|---|---|---|
| WO | WO-99/54359 A1 | 10/1999 |
| WO | WO-2004/018499 A2 | 3/2004 |
| WO | WO 2008063424 A2 * | 5/2008 |

OTHER PUBLICATIONS

UniProt Database Accession No. Q5RK13, Feb. 2005, 2 pages.*
UniProt Database Accession No. Q5U743, Feb. 2005, 1 page.*
Dictionary.com definition of "infuse", 1 page, last viewed on Jan. 18, 2017.*
Abraham et al., "Heparin-binding EGF-like growth factor: characterization of rat and mouse cDNA clones, protein domain conservation across species, and transcript expression in tissues," Biochem Biophys Res Commun. 190(1):125-33 (1993).
Ballard et al., "Binding properties and biological potencies of insulin-like growth factors in L6 myoblasts," Biochem J. 233(1):223-30 (1986).
Brittberg et al., "Treatment of deep cartilage defects in the knee with autologous chondrocyte transplantation," N Engl J Med. 331(14):889-95 (1994).
Ceuninck et al.,"High binding capacity of cyclophilin B to chondrocyte heparan sulfate proteoglycans and its release from the cell surface by matrix metalloproteinases: possible role as a proinflammatory mediator in arthritis," Arthritis Rheum. 48(8):2197-206 (2003).
Chevalier et al., "Production of Binding Proteins and Role of the Insulin-Like Growth Factor I Binding Protein 3 in Human Articular Cartilage Explants," British J Rheumatol. 35:515-522 (1996).
Communication Pursuant to Article 94(3) EPC issued in European Patent Application No. 07867389, dated Apr. 4, 2011 (4 pages).
Communication Pursuant to Article 94(3) EPC issued in Europoean Patent Application No. 07867389, dated Aug. 8, 2011 (3 pages).

(Continued)

*Primary Examiner* — David Steadman
(74) *Attorney, Agent, or Firm* — Clark & Elbing LLP

(57) ABSTRACT

The present invention is directed to proteins in which a heparin binding peptide is fused to a growth factor that promotes cell growth and survival. The compound thus formed is bound to the surface of cells which are then administered to damaged tissue. The growth factor is thereby maintained at the site of administration where it promotes repair.

10 Claims, No Drawings

(56) References Cited

OTHER PUBLICATIONS

Communication Pursuant to Article 94(3) EPC issued in Europoean Patent Application No. 07867389, dated Feb. 25, 2010 (1 page).
Congote, "Increased heparin binding by site directed mutagenesis of a recombinant chimera of bombyxin and insulin-like growth factor II," Biochimica et Biophysica Acta 1243:538-542 (1995).
Davis et al., "Local myocardial insulin-like growth factor I (IGF-1) delivery with biotinylated peptide nanofibers improves cell therapy for myocardial infarction," PNAS 103(21):8155-8160 (May 2006).
International Preliminary Report on Patentability for PCT/US2007/023527, dated May 19, 2009 (7 pages).
International Search Report for PCT/US07/23527 dated Jun. 19, 2008 (2 pages).
Kofidis et al., "Insulin-Like Growth Factor Promotes Engraftment, Differentiation, and Functional Improvement after Transfer of Embryonic Stem Cells for Myocardial Restoration," Stem Cells 22:1239-1245 (2004).
Li et al., "Overexpression of Insulin-like Growth Factor-1 in Mice Protects from Myocyte Death after Infarction, Attenuating Ventricular Dilation, Wall Stress, and Cardiac Hypertrophy," J. Clin. Invest. 100:1991-1999 (Oct. 1997).
Ozdinler et al., "IGF-1 Specifically Enhances Axon Outgrowth of Corticospinal Motor Neurons," Nature Neurosci. 9:1371-1381 (Nov. 2006).
Palmen et al., "Cardiac Remodeling after Myocardial Infarction is Impaired in IGF-1 Deficient Mice," Cardiovasc. Res. 50:516-524 (2001).
Schmidt et al., "A review of the effects of insulin-like growth factor and platelet derived growth factor on in vivo cartilage healing and repair," OsteoArthritis and Cartilage 14:403-412 (2006).
Search Report prepared by the Hungarian Patent Office for Singapore Application No. 2009031444, dated Jun. 10, 2010.
Segev et al., "The role of perlecan in arterial injury and angiogenesis," Cardiovascular Res. 63:603-610 (2004).
Supplementary European Search Report for Application No. EP 07 86 7389, dated Oct. 29, 2009 (12 pages).
Thompson et al., "Characterization of Sequences within Heparin-binding EGF-like Growth Factor That Mediate interaction with Heparin," J Biol Chem. 269(4):2541-2549 (Jan. 1994).
Tokunou et al., "Abstract 1269: Engineering a New Insulin-Like Growth Factor-1 Protein for Embryonic Stem Cell Therapy," Circulation 114(18 Suppl. S):239 (2006).
Tokunou et al., "Engineering insulin-like growth factor-1 for local delivery," FASEB J. 22(6):1886-93 (2008).
Torella et al., "Cardiac Stem Cell and Myocyte Aging, Heart Failure, and Insulin-Like Growth Factor-1 Overexpression," Circ. Res. 94:514-524 (2004).
Vasan et al., "Serum Insulin-like Growth Factor I and Risk for Heart Failure in Elderly Individuals Without a Previous Myocardial Infarction: The Framingham Heart Study," Ann. Intern. Med. 139:642-648 (2003).
Vig et al., "Intranasal administration of IGF-I improves behavior and Purkinje cell pathology in SCA1 mice," Brain Research Bulletin 69:573-579 (2006).
Vincent et al., "Basic FGF mediates an immediate response of articular cartilage to mechanical injury," PNAS 99(12):8259-8264 (2002).
Wilczak et al., "Insulin-Like Growth Factor System in Amyotrophic lateral Sclerosis," Endocr. Dev. 9: 160-169 (2005).
Written Opinion of the International Searching Authority for PCT/US07/23527 dated Jun. 19, 2008 (6 pages).
Written Opinion prepared by the Hungarian Patent Office for Singapore Application No. 2009031444, dated Jun. 10, 2010.
Zhang et al., "Design of Nanostructured Biological Materials Through Self-Assembly of Peptides and Proteins," Curr. Opin. Chem. Biol. 6:865-871 (2002).
Zhang et al., "Spontaneous Assembly of a Self-Complementary Oligopeptide to Form a Stable Macroscopic Membrane," Proc. Natl. Acad. Sci. USA 90:3334-3338 (Apr. 1993).
Declaration of Dr. Parth Patwari from U.S. Appl. No. 11/979,708, dated Mar. 5, 2013 (9 pages).
Miller et al., "Intraarticular injection of heparin-binding insulin-like growth factor 1 sustains delivery of insulin-like growth factor 1 to cartilage through binding to chondroitin sulfate," Arthritis Rheum. 62(12):3686-3694 (2010).
Loffredo et al., "Targeted delivery to cartilage is critical for in vivo efficacy of insulin-like growth factor 1 in a rat model of osteoarthritis," Arthritis Rheumatol. 66(5):1247-55 (2014).
Fisher et al., "Heparan sulfate proteoglycans including syndecan-3 modulate BMP activity during limb cartilage differentiation," Matrix Biol. 25(1):27-39 (2006).
Ruppert et al., "Human bone morphogenetic protein 2 contains a heparin-binding site which modifies its biological activity," Eur J Biochem. 237(1):295-302 (1996).

* cited by examiner

```
                              SEQUENCE LISTING

<160> NUMBER OF SEQ ID NOS: 24

<210> SEQ ID NO 1
<211> LENGTH: 153
<212> TYPE: PRT
<213> ORGANISM: Homo sapiens

<400> SEQUENCE: 1

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
                20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
                100                 105                 110

Lys Pro Ala Lys Ser Ala Arg Ser Val Arg Ala Gln Arg His Thr Asp
            115                 120                 125

Met Pro Lys Thr Gln Lys Glu Val His Leu Lys Asn Ala Ser Arg Gly
        130                 135                 140

Ser Ala Gly Asn Lys Asn Tyr Arg Met
145                 150

<210> SEQ ID NO 2
<211> LENGTH: 69
<212> TYPE: PRT
<213> ORGANISM: Homo sapiens

<400> SEQUENCE: 2

Pro Glu Thr Leu Cys Gly Ala Glu Leu Val Asp Ala Leu Gln Phe Val
1               5                   10                  15

Cys Gly Pro Arg Gly Phe Tyr Phe Asn Lys Pro Thr Gly Tyr Gly Ser
                20                  25                  30

Ser Ile Arg Arg Ala Pro Gln Thr Gly Ile Val Asp Glu Cys Cys Phe
            35                  40                  45

Arg Ser Cys Asp Leu Arg Arg Leu Glu Met Tyr Cys Ala Pro Leu Lys
        50                  55                  60

Pro Thr Lys Ser Ala
65

<210> SEQ ID NO 3
<211> LENGTH: 22
<212> TYPE: PRT
<213> ORGANISM: Homo sapiens

<400> SEQUENCE: 3

Lys Lys Lys Arg Lys Gly Lys Gly Leu Gly Lys Lys Arg Asp Pro Cys
1               5                   10                  15
```

Leu Lys Lys Tyr Lys Gly
            20

<210> SEQ ID NO 4
<211> LENGTH: 17
<212> TYPE: PRT
<213> ORGANISM: Homo sapiens

<400> SEQUENCE: 4

Arg Ile Gln Asn Leu Leu Lys Ile Thr Asn Leu Arg Ile Lys Phe Val
1               5                   10                  15

Lys

<210> SEQ ID NO 5
<211> LENGTH: 20
<212> TYPE: PRT
<213> ORGANISM: Homo sapiens

<400> SEQUENCE: 5

Pro Tyr Val Val Leu Pro Arg Pro Val Cys Phe Glu Lys Gly Met Asn
1               5                   10                  15

Tyr Thr Val Arg
            20

<210> SEQ ID NO 6
<211> LENGTH: 22
<212> TYPE: PRT
<213> ORGANISM: Homo sapiens

<400> SEQUENCE: 6

Lys Gln Asn Cys Leu Ser Ser Arg Ala Ser Phe Arg Gly Cys Val Arg
1               5                   10                  15

Asn Leu Arg Leu Ser Arg
            20

<210> SEQ ID NO 7
<211> LENGTH: 25
<212> TYPE: PRT
<213> ORGANISM: Homo sapiens

<400> SEQUENCE: 7

Lys Asp Gly Arg Lys Ile Cys Leu Asp Leu Gln Ala Pro Leu Tyr Lys
1               5                   10                  15

Lys Ile Ile Lys Lys Leu Leu Glu Ser
            20                  25

<210> SEQ ID NO 8
<211> LENGTH: 22
<212> TYPE: PRT
<213> ORGANISM: Homo sapiens

<400> SEQUENCE: 8

Cys Lys Asn Gly Gly Phe Phe Leu Arg Ile Ala Pro Asp Gly Arg Val
1               5                   10                  15

Asp Gly Val Arg Glu Lys
            20

<210> SEQ ID NO 9
<211> LENGTH: 31
<212> TYPE: PRT
<213> ORGANISM: Homo sapiens

<400> SEQUENCE: 9

Tyr Ser Ser Trp Tyr Val Ala Leu Lys Arg Thr Gly Gln Tyr Lys Leu
1               5                   10                  15

Gly Pro Lys Thr Gly Pro Gly Gln Lys Ala Ile Leu Phe Leu Pro
            20                  25                  30

<210> SEQ ID NO 10
<211> LENGTH: 27
<212> TYPE: PRT
<213> ORGANISM: Homo sapiens

<400> SEQUENCE: 10

Ala Lys Leu Asn Cys Arg Leu Tyr Arg Lys Asn Lys Ser Ser Lys
1               5                   10                  15

Leu Val Ser Ala Asn Arg Leu Phe Gly Asp Lys
            20                  25

<210> SEQ ID NO 11
<211> LENGTH: 23
<212> TYPE: PRT
<213> ORGANISM: Homo sapiens

<400> SEQUENCE: 11

Leu Arg Lys Leu Arg Lys Arg Leu Leu Arg Asp Ala Asp Asp Leu Gln
1               5                   10                  15

Lys Arg Leu Ala Val Tyr Gln
            20

<210> SEQ ID NO 12
<211> LENGTH: 42
<212> TYPE: PRT
<213> ORGANISM: Homo sapiens

<400> SEQUENCE: 12

Pro Leu Gln Glu Arg Ala Gln Ala Ala Trp Gln Glu Arg Leu Arg Ala
1               5                   10                  15

Arg Met Glu Glu Met Gly Ser Arg Thr Arg Asp Arg Leu Asp Glu Val
            20                  25                  30

Lys Glu Gln Val Ala Glu Arg Ala Lys Leu
        35                  40

<210> SEQ ID NO 13
<211> LENGTH: 10
<212> TYPE: PRT
<213> ORGANISM: Homo sapiens

<400> SEQUENCE: 13

Lys Gly Lys Met His Lys Thr Cys Tyr Tyr
1               5                   10

<210> SEQ ID NO 14
<211> LENGTH: 10
<212> TYPE: PRT
<213> ORGANISM: Homo sapiens

<400> SEQUENCE: 14

Met Gly Lys Met His Lys Thr Cys Tyr Asn
1               5                   10

<210> SEQ ID NO 15
<211> LENGTH: 28
<212> TYPE: PRT
<213> ORGANISM: Homo sapiens

<400> SEQUENCE: 15

Pro Pro Thr Ile Ile Trp Lys His Lys Gly Arg Asp Val Ile Leu Lys
1               5                   10                  15

Lys Asp Val Arg Phe Ile Val Leu Ser Asn Asn Tyr
            20                  25

<210> SEQ ID NO 16
<211> LENGTH: 22
<212> TYPE: PRT
<213> ORGANISM: Homo sapiens

<400> SEQUENCE: 16

Lys Lys His Glu Ala Lys Asn Trp Phe Val Gly Leu Lys Lys Asn Gly
1               5                   10                  15

Ser Cys Lys Arg Gly Pro
            20

<210> SEQ ID NO 17
<211> LENGTH: 32
<212> TYPE: PRT
<213> ORGANISM: Homo sapiens

<400> SEQUENCE: 17

Lys Gly Gly Arg Gly Thr Pro Gly Lys Pro Gly Pro Arg Gly Gln Arg
1               5                   10                  15

Gly Pro Thr Gly Arg Gly Glu Arg Gly Pro Arg Gly Ile Thr Gly Lys
            20                  25                  30

<210> SEQ ID NO 18
<211> LENGTH: 12
<212> TYPE: PRT
<213> ORGANISM: Homo sapiens

<400> SEQUENCE: 18

Gly Glu Phe Tyr Asp Leu Arg Leu Lys Gly Asp Lys
1               5                   10

<210> SEQ ID NO 19
<211> LENGTH: 15
<212> TYPE: PRT
<213> ORGANISM: Homo sapiens

<400> SEQUENCE: 19

His Arg His His Pro Arg Glu Met Lys Lys Arg Val Glu Asp Leu
1               5                   10                  15

<210> SEQ ID NO 20
<211> LENGTH: 14
<212> TYPE: PRT
<213> ORGANISM: Homo sapiens

<400> SEQUENCE: 20

Glu Lys Thr Leu Arg Lys Trp Leu Lys Met Phe Lys Lys Arg
1               5                   10

<210> SEQ ID NO 21
<211> LENGTH: 19
<212> TYPE: PRT
<213> ORGANISM: Homo sapiens

<400> SEQUENCE: 21

Ala Glu Ala Ala Ala Arg Ala Ala Ala Arg Arg Ala Arg Ala

```
1               5                  10                 15
Ala Ala Arg

<210> SEQ ID NO 22
<211> LENGTH: 20
<212> TYPE: DNA
<213> ORGANISM: Rattus norvegicus

<400> SEQUENCE: 22
ggaccagagg accctttgcg                                              20

<210> SEQ ID NO 23
<211> LENGTH: 22
<212> TYPE: DNA
<213> ORGANISM: Rattus norvegicus

<400> SEQUENCE: 23
agctgacttt gtaggcttca gc                                           22

<210> SEQ ID NO 24
<211> LENGTH: 63
<212> TYPE: PRT
<213> ORGANISM: Rattus norvegicus

<400> SEQUENCE: 24

Ala Ala Ala Ala Ala Gly Ala Ala Gly Ala Gly Gly Ala Ala Gly
1               5                  10                 15

Gly Cys Ala Ala Gly Gly Gly Gly Thr Thr Ala Gly Gly Ala Ala Ala
            20                 25                 30

Gly Ala Ala Gly Ala Gly Ala Gly Ala Thr Cys Cys Ala Thr Gly Cys
        35                 40                 45

Cys Thr Thr Ala Ala Gly Ala Ala Ala Thr Ala Cys Ala Ala Gly
        50                 55                 60
```

METHODS OF TREATING DAMAGED CARTILAGE TISSUE USING GROWTH FACTORS FUSED TO HEPARIN BINDING SEQUENCES

CROSS REFERENCE TO RELATED APPLICATIONS

The present application claims priority to, and the benefit of, U.S. provisional application 60/858,406, filed on Nov. 13, 2006, the contents of which is hereby incorporated by reference in its entirety.

FIELD OF THE INVENTION

The present invention is directed to proteins in which a polypeptide that promotes the growth and/or survival of cells is fused to a peptide that binds to heparin. These proteins may be bound to cardiomyocytes and administered to damaged cardiac tissue to help promote repair.

BACKGROUND OF THE INVENTION

Insulin like growth factor-1 (IGF-1) is a protein that promotes the growth and survival of cardiomyocytes. Mice deficient in IGF-1 exhibit increased apoptosis following myocardial infarction (Palmen, et al., *Cardiovasc. Res.* 50:516-524 (2001)), whereas cardiac-specific IGF-1 overexpression protects against myocyte apoptosis and ventricular dilation following infarction (Li, et al., *J. Clin. Invest.* 100:1991-1999 (1997); Torella, et al., *Circ. Res.* 94:514-524 (2004)). IGF-1 overexpression also increases cardiac stem cell number and growth, leading to an increase in myocyte turnover and function in the aging heart. Following infarction, IGF-1 promotes engraftment, differentiation, and functional improvement of embryonic stem cells transplanted into myocardium (Kofidis, et al., *Stem Cells* 22:1239-1245 (2004)). In addition, serum levels of IGF-1 correlate inversely with the risk of congenital heart failure in a subset of elderly patients (Vasan, et al., *Ann. Intern. Med.* 139:642-648 (2003)).

The characteristics described above make IGF-1 an attractive therapeutic agent for patients that have experienced damage to cardiac tissue, e.g., patients that have undergone a myocardial infarction. However, IGF-1 is a small protein that diffuses readily through tissues. As a result, it is difficult to keep a high concentration of this factor at a site of tissue damage for a prolonged period of time. One approach that has been taken to maintain a high local concentration is to attach IGF-1 to a self-assembling biological membrane (see US20060088510). Using a rat model of myocardial infarction, it was found that when this membrane is implanted along with neonatal cardiomyocytes, the survival and growth of the implanted cells is improved relative to cells implanted with unbound IGF-1. Thus, the ability of the cells to colonize the damaged heart and improve function is increased. Using a similar approach, positive results were also obtained using PDGF (US20060148703). Although these results are promising, alternative procedures that avoid the necessity of constructing and implanting membranes would be desirable.

SUMMARY OF THE INVENTION

The present invention is based upon the development of a procedure for binding IGF-1 to cardiomyocytes prior to their implantation into damaged cardiac tissue. It has been found that it is possible to join IGF-1 to a heparin binding peptide (HBP) and obtain a fusion protein that maintains a beneficial effect on the survival of cultured cells. The fusion protein binds to cardiomyocytes (presumably to cell surface heparin) better than IGF-1 alone. Since many different cell types have cell surface heparin, it is not expected that simply injecting the IGF-1/HBP protein systemically would be of much benefit to cardiac patients. However, targeting may be achieved by incubating cardiomyocytes with IGF-1/HBP prior to implantation. To a lesser extent, localization may also be achieved by injecting the protein directly into cardiac tissue. Similar approaches should be useful in treating other conditions (e.g., wounds) that respond to growth factors (with or without the transplantation of cells).

In its first aspect, the invention is directed to a compound having the formula: $B\text{-}(J)_n\text{-}(Z)_q$, or $(Z)_q\text{-}(J)_n\text{-}B$, where n is an integer from 0-10; q is an integer from 1-5; B is a peptide that promotes the growth and/or survival of cardiomyocytes (as determined, e.g., using cells deprived of serum) and Z is a heparin binding peptide. Any of the heparin binding peptides known in the art may be used including all of the peptides described herein. J is either a proteinogenic amino acid or compounds such as biotin/avidin that can be used to join peptides together. For the purposes of the present invention, all peptide sequences are written from the N terminus (far left) to the C terminus (far right) and unless otherwise indicated, all peptides are made up of "proteinogenic" amino acids, i.e., they are the L-isomers of: alanine (A); arginine (R); asparagine (N); aspartic acid (D); cysteine (C); glutamic acid (E); glutamine (Q); glycine (G); histidine (H); isoleucine (I); leucine (L); lysine (K); methionine (M); phenylalanine (F); proline (P); serine (S); threonine (T); tryptophan (W); tyrosine (Y); or valine (V).

In preferred embodiments, the compound of the formulas shown above is a fusion protein in which J is a proteinogenic amino acid and B is either insulin like growth factor-I (IGF-1) or platelet derived growth factor (PDGF). The full length sequence for human IGF-1 (GenBank Accession No. NM 00618) is as follows:

```
                                            (SEQ ID NO: 1)
MGKISSLPTQLFKCCFCDFLKVKMHTMSSSHLFYLALCLLTFTSSATAGP

ETLCGAELVDALQFVCGDRGFYFNKPTGYGSSSRRAPQTGIVDECCFRSC

DLRRLEMYCAPLKPAKSARSVRAQRHTDMPKTQKEVHLKNASRGSAGNKN

YRM.
```

However, the underlined sequence is sufficient for the promotion of cardiomyocyte growth and survival in accordance with the procedures described herein. Thus, for the purposes of the present invention, IGF-1 is defined as having the core sequence: PETLCGAELVDALQFVCGPRGFYFNKPT-GYGSSIRRAPQTGIVDECCFRSCDLRRLEMYCA-PLKPTKSA (SEQ ID NO:2) and may optionally include any additional portion of the sequence of SEQ ID NO:1. For example, the C terminus may begin with G, AG, TAG etc. Similarly the N terminus of SEQ ID NO:2 may be extended in accordance with SEQ ID NO: 1. Thus, the peptide may terminate in R, RS, RSV etc. The full length amino acid sequence of PDGF is also well known in the art (see, Rao, et al., *Proc. Nat'l Acad. Sci. USA* 83:2392-2396 (1986)) and may be found, inter alia, as GenBank accession number P01127. In the formulas presented above, n is preferably 0 and q is preferably 1.

Preferred heparin binding peptides, i.e. Z in the formulas, are:

KKKRKGKGLGKKRDPCLKKYKG; (SEQ ID NO: 3)

RIQNLLKITNLRIKFVK; (SEQ ID NO: 4)

PYVVLPRPVCFEKGMNYTVR; (SEQ ID NO: 5)

KQNCLSSRASFRGCVRNLRLSR; (SEQ ID NO: 6)

KDGRKICLDLQAPLYKKIIKKLLESL (SEQ ID NO: 7)

CKNGGFFLRIAPDGRVDGVREK; (SEQ ID NO: 8)

YSSWYVALKRTGQYKLGPKTGPGQKAILFLP; (SEQ ID NO: 9)

AKLNCRLYRKANKSSKLVSANRLFGDK; (SEQ ID NO: 10)

LRKLRKRLLRDADDLQKRLAVYQ; (SEQ ID NO: 11)

PLQERAQAAWQERLRARMEEMGSRTRDRLDEVKEQVAERAKL; (SEQ ID NO: 12)

KGKMHKTCYY; (SEQ ID NO: 13)

MGKMHKTCYN; (SEQ ID NO: 14)

PPTIIWKHKGRDVILKKDVRFIVLSNNY; (SEQ ID NO: 15)

KKHEAKNWFVGLKKNGSCKRGP; (SEQ ID NO: 16)

KGGRGTPGKPGPRGQRGPTGRGERGPRGITGK; (SEQ ID NO: 17)

GEFYDLRLKGDK; (SEQ ID NO: 18)

HRHHPREMKKRVEDL; (SEQ ID NO: 19)

EKTLRKWLKMFKKR; (SEQ ID NO: 20)
and

AEAAARAAARRAARRAAAR. (SEQ ID NO: 21)

The invention also includes DNA molecules encoding any of the fusion proteins described above, vectors containing these DNA molecules and host cells transformed with the vectors. The host cells may be used to produce the fusion proteins for use in the therapeutic methods described herein. The DNA may also be used to transform cells that secrete the fusion protein at the site of tissue damage. Once secreted, the proteins should bind to other cells in the vicinity, thereby maintaining a relatively high localized concentration.

The invention also includes methods of treating patients for any condition responsive to IGF-1 or PDGF using one or more of the fusion proteins or compounds. In one embodiment, the compounds or fusion proteins are administered directly to the treatment site to allow them to bind to the surfaces of endogenous cells. More preferably, they are used in treating conditions where tissue growth or repair is needed and there are cells available that can be used to aid this process. In these cases, the compounds or fusion proteins will be preincubated with the cells to allow them to bind prior to implantation. In a particularly preferred method, a patient is treated for damaged cardiac tissue (e.g., due to a myocardial infarction) by incubating cardiomyocytes with the compounds or fusion proteins for a period of time and under conditions sufficient to permit them to bind. The cells are then injected or implanted into the cardiac tissue of the patient.

The compounds and fusion proteins may also be used to repair damaged cartilage. Normally, IGF-1 diffuses out of cartilage and its effect on transplanted chondrocytes is therefore reduced or lost. By incubating the chondrocytes with heparin-binding IGF-1 prior to implantation, the local concentration of the growth factor will be increased and, as a result, the chondrocytes will make more cartilage.

Growth factors engineered to bind heparin, particularly IGF-1, may also be bound to cells being implanted to repair and regenerate neurons, e.g., in patients with neurodegenerative diseases such as ALS, who have had a stroke, or who have lost nerve function as the result of an injury. IGF-1 is a candidate for clinical trials in ALS and has been found to promote axon outgrowth in corticospinal motor neurons (Özdinler, et al., Nature Neurosci. 9:1371-1381 (2006)). By binding the IGF-1 to the neurons before implantation, their growth in vivo will be enhanced.

DESCRIPTION OF THE INVENTION

The present invention is based upon the concept that that the recovery of tissue after injury is promoted by maintaining high local concentrations of growth factors such as IGF-1 or PDGF. Experiments described in the art have supported this approach using biologically compatible membranes to retain therapeutic agents at the site of administration (see US20060088510 and US20060148703). It has now been discovered that growth factors can be fused to heparin binding peptides and bound to cardiomyocytes prior to their implantation into the heart tissue. The fused protein maintains its ability to promote cell growth and survival and is maintained at the site of implantation without the need to make and use a biologically compatible membrane.

Making of Peptides

One way of joining the heparin binding peptide to the therapeutic agent is through the use of a nonpeptide linker. For example, the use of biotin and avidin for linking molecules is well known in the art and standard methodology can be used for attaching heparin binding peptides to growth factors such as IGF-1. In order to prevent steric interference between the biotin/avidin groups and peptides, a spacer may be included between the two. The spacer can take the form of 1-15 (preferably 1-10) fatty acids or 1-15 (preferably 1-10) amino acids. Methodology for incorporating spacers of this type is well known in the art.

Preferably, heparin binding peptides and growth factors such as IGF-1 and PDGF are joined together in the form of a fusion protein. Fusion proteins may either be chemically synthesized or made using recombinant DNA techniques. Chemical methods include solid-phase peptide synthesis using standard N-tert-butyoxycarbonyl (t-Boc) chemistry and cycles using n-methylpyrolidone chemistry. Once peptides have been synthesized, they can be purified using procedures such as high pressure liquid chromatography on reverse-phase columns. Purity may also be assessed by HPLC and the presence of a correct composition can be determined by amino acid analysis.

Binding to Cells

Cardiomyocytes or other cells may be obtained using standard procedures and may then be incubated with fusion compositions or proteins for a period sufficient to allow the fusion proteins to bind to cell surfaces. The incubation may last anywhere from about an hour to several days and should be carried out under conditions that allow for cell survival, e.g. at about 37° C., neutral pH, and in a culture medium that insures cell survival. The amount of protein present should generally be enough to coat the cells but the exact amount is not critical. The cells may be administered by syringe or catheter to cardiac tissue. The exact amount of cells used is not critical but, in general, between $1 \times 10^5$ and $1 \times 10^7$ will be used.

Pharmaceutical Compositions and Dosages

Fusion proteins may be incorporated into a pharmaceutical composition containing a carrier such as saline, water, Ringer's solution and other agents or excipients and cells may be maintained in standard media to maintain viability. Preparations will generally be designed for implantation, infusion or injection, particularly into cardiac tissue but topical treatments will also be useful, e.g., in the treatment of wounds. All pharmaceutical compositions may be prepared using methods that are standard in the art (see e.g., *Remington's Pharmaceutical Sciences*, 16th ed. A. Oslo. ed., Easton, Pa. (1980)).

It is expected that the skilled practitioner will adjust dosages on a case by case basis using methods well established in clinical medicine. The optimal dosage will be determined by methods known in the art and will be influenced by factors such as the age of the patient, disease state and other clinically relevant factors.

EXAMPLES

Example 1

Survival of Cardiomyocytes

The present example demonstrates that IGF-1 improves survival of ES-derived cardiomyocytes and describes the development of a novel heparin binding (HB)-IGF-1 fusion protein engineered to improve survival of injected cells.

Methods and Results

To minimize teratoma formation, we studied ES cells committed to the cardiomyocyte lineage. Mouse ES cells, stably transfected with α-cardiac myosin heavy chain promoter-driven enhanced green fluorescent protein (EGFP), were differentiated into cardiomyocytes by the hanging drop method and EGFP positive cells were purified by fluorescent cell sorting. In these ES-derived cardiomyocytes, IGF-1 reduced cell death induced by serum deprivation, (13.6+/−1.9% vs 25.9+/−2.5% in control, $p<0.05$) and decreased apoptosis induced by serum deprivation (TUNEL-positive cells 8.0+/−1.5% to 4.3+/−0.5% respectively, $p<0.05$). Furthermore, IGF-1 decreased Doxorubicin (1 µM, 24 hr) or chelerythrin (3 µM, 1 hr)-induced apoptosis ($p<0.01$). The phosphoinositide-3 kinase inhibitor, LY294002 (10 µM), inhibited the protective effect of IGF-1 on Doxorubicin-induced apoptosis ($p<0.05$). Since IGF-1 diffuses rapidly away from injected sites, we then designed and expressed a novel recombinant IGF-1 fusion protein with an N-terminal HB domain. The protein was purified by Nickel-affinity chromatography and then subjected to oxidative refolding to restore biological activity. HB-IGF-1 bound to cell surfaces dramatically better than IGF-1 and HB-IGF-1 activated Akt in neonatal cardiac myocytes and 3T3 fibroblasts as potently as native IGF-1.

Conclusions

Because IGF-1 improves survival of ES-derived cardiomyocytes in vitro, this new Heparin-binding IGF-1 should improve cell therapy by binding to the surfaces of injected cells. This demonstrates the potential for changing the cellular microenvironment through locally-delivered therapeutic proteins.

Example 2

Cartillage Repair

In this example, we designed and purified a novel protein, Heparin-binding IGF-1 (HB-IGF-1), which is a fusion protein of native IGF-1 with the heparin-binding domain of Heparin-binding epidermal growth factor-like growth factor. HB-IGF-1 bound selectively to heparin as well as the cell surfaces of 3T3 fibroblasts, neonatal cardiac myocytes and differentiating embryonic stem cells. HB-IGF-1 activated the IGF-1 receptor and Akt with the identical kinetics and dose-dependence of IGF-1, indicating no compromise of biological activity due to the heparin-binding domain. Because cartilage is a proteoglycan-rich environment and IGF-1 is a known stimulus for chondrocyte biosynthesis, we then studied the effectiveness of HB-IGF-1 in cartilage. HB-IGF-1 was selectively retained by cartilage explants and led to sustained chondrocyte proteoglycan biosynthesis compared to IGF-1. These data show that the strategy of engineering a "long-distance" growth factor like IGF-1 for local delivery may be useful for tissue repair and minimizing systemic effects.

Material and Methods

Vector Construction

Rat IGF-1 cDNA was amplified by Polymerase chain reaction (PCR) using primers (5' to 3') GGACCAGAG-GACCCTTTGCG (forward, SEQ ID NO:22) and AGCT-GACTTTGTAGGCTTCAGC (reverse, SEQ ID NO:23). We used mature peptide IGF-1 (70 amino acids), which encodes exons 3 and 4 (Hameed, et al., *J. Physiol.* 547:247-254 (2003); Shavlakadze, et al., *Growth Horm IGF Res* 15:4-18 (2005); Musaro, et al., *Exp Gerontol* 42:76-80 (2007)). The product was subcloned into the pTrcHis-TOPO vector (Invitrogen, Carlsbad, Calif., USA) with the addition of a stop codon (TAG) at the C-terminus of IGF-1, thus encoding an Xpress-tagged IGF-1 (Xpress-IGF-1). To encode HB-IGF-1, the heparin binding sequence (AA 93-113) of rat HB-EGF(AAAAAGAAGAG-GAAAGGCAAGGGGTTAGGAAAGAAGAGAGATC-CATGCCTTAAGAAATACAAG (SEQ ID NO:24)) was inserted between the X-press tag and the IGF-1 sequence through mutagenesis.

Amplification was performed with PfuUltra HF DNA Polymerase (Stratagene, Cedar Creek, Tex., USA) and the template plasmid was digested with DpnI (New England Biolabs, Beverly, Mass., USA) before transformation in *E. coli*. All sequences were confirmed by DNA sequencing.

Purification of Protein

Xpress-IGF-1 and HB-IGF-1 were expressed in *E. coli* BL21 cells and grown in LB medium in 4 1 batches. Protein synthesis was induced with 1 mM isopropyl β-D-thiogalactoside for 4 hours and cells were then harvested by centrifugation, lysed in lysis buffer (6 M guanidine hydrochloride, 20 mM sodium phosphate, 500 mM NaCl, pH 7.8) and homogenized. The first purification step consisted of affinity purification by the polyhistidine tag in fusion proteins with Ni-NTA (Invitrogen). Ni-NTA resin was washed with wash buffer (8 M urea, 500 mM NaCl, 20 mM phosphate, pH 6.2), and bound protein was eluted at pH 4. Eluted proteins were then subjected to oxidative refolding to restore biological activity. The proteins were incubated overnight at 4° C. with refolding buffer (50 mM Tris, 75 mM NaCl, 100 µM oxidized-glutathione and 100 μM reduced-glutathione, pH 7.8). After refolding, the samples were adjusted to 0.1% trifluoroacetic acid and loaded on a C18 reverse-phase high-performance liquid chromatography (RP-HPLC) column (Delta-Pak C18, Waters, Milford, Mass., USA) as a final purification step. The column was subjected to a linear gradient from 25% to 40% acetonitrile in 0.1% trifluoroacetic acid.

Cell Culture

Primary cultures of cardiac myocytes were prepared from the ventricles of neonatal Sprague Dawley rats and cultured in Dulbecco's modified Eagle's medium (DMEM, Invitrogen) with 7% fetal bovine serum (Invitrogen); medium was replaced after 24 hours with serum-free medium. 3T3 fibroblast cells were cultured in DMEM with 10% newborn calf serum (Invitrogen) and the medium was replaced with serum-free medium 24 hours before experiments. Mouse embryonic stem (ES) cells were grown on gelatin-coated dishes without feeder cells in Glasgow Minimum Essential Medium (Invitrogen) supplemented with 15% KNOCKOUT SR (Invitrogen) and leukemia inhibitory factor (Chemicon, Billerica, Mass., USA). Cells were passaged every three days. To induce differentiation, cells were first enzymatically dissociated and cultured as hanging drops for embryoid body formation as described previously (Takahashi, et al., *Circulation* 107:1912-1916 (2003)). Differentiation medium with 10% ES cell-qualified fetal bovine serum (Invitrogen) without leukemia inhibitory factor was added. These ES cells become green fluorescent protein (GFP) positive after differentiation into cardiac myocytes, because they were stably transfected with an alpha-Myosin heavy chain promoter-driven enhanced GFP vector. After embryoid body formation (days 7), cells were plated on gelatin-coated dishes.

Harvest and Culture of Cartilage

Bovine articular cartilage explants (3-mm-diameter, 1-mm-thick disks) were harvested from the femoropatellar grooves of 1-2-week-old calves and cultured in low-glucose DMEM with 10 mM HEPES, 0.1 mM nonessential amino acids, 0.4 mM L-proline, 20 μg/ml ascorbate, 100 U/ml penicillin and 100 μg/ml streptomycin at 37° C. in a 5% $CO_2$ atmosphere.

Protein Analysis

Neonatal cardiac myocytes and 3T3 fibroblasts were lysed using phosphate-buffered saline (PBS) with 1% Triton-X, 0.25% Na-deoxycholate, 1 mM ethylenediamine-tetraacetic acid (EDTA), 1 mM phenylmethylsulfonyl fluoride (PMSF), 1 mM NaF, 1 mM $Na_3VO_4$ and 1:1000 protease inhibitor cocktail (Sigma, St. Louis, Md., USA). Cartilage disks were pulverized and lysed with 100 mM NaCl, 50 mM Tris, 0.5% Triton-X, 5 mM EDTA, 1 mM PMSF and 1:1000 proteinase inhibitor cocktail (Sigma). Protein concentration was measured by Bradford assay and 10 μg protein was loaded in each well for Western blot analysis. Similar GAG content was observed in all samples as measured by DMMB dye binding. Anti-Xpress antibody (Invitrogen), anti-polyclonal IGF-1 antibody (Abcam, Cambridge, Mass., USA), anti-phospho-IGF-1 receptor antibody (Cell Signaling, Danvers, Mass., USA), anti-phospho-Akt antibody (Cell Signaling) and anti-Actin antibody (Sigma) were used. IGF-1 was purchased from Sigma as a control protein.

To detect the fusion proteins by enzyme-linked immunosorbent assays (ELISA), 96-well plates were coated with an anti-Xpress antibody (10 μl/ml) overnight. Identical amounts of protein from cartilage extracts were added to each well. Polyclonal IGF-1 antibody was used as the primary antibody, and anti-rabbit-horseradish peroxidase (Bio-Rad, Hercules, Calif., USA) was used as the secondary antibody. After addition of ABTS Peroxidase Substrate (KPL, Gaithersburg, Md., USA), plates were read at 405 nm.

Binding Assays

Heparin agarose beads (Sigma) were incubated with 300 pmol HB-IGF-1 or Xpress-IGF-1 or 2 hours and washed 3 times with PBS. Bound fusion proteins with Heparin agarose beads were extracted by boiling with SDS-PAGE sample buffer (Invitrogen). 3T3 fibroblast cells or neonatal rat cardiomyocytes were incubated with 100 nM HB-IGF-1 or control IGF-1 (Sigma) for 2 hours and then washed with PBS 3 times. The cells were lysed with lysis buffer and then subjected to Western blot analysis with an anti-IGF-1 antibody. Embryoid bodies (10 days after induction of differentiation) were incubated with fusion proteins for 2 hours, washed with PBS 3 times, and fixed with paraformaldehyde before immunohistochemistry with an anti-Xpress antibody. Cartilage disks were cultured in serum-free DMEM supplemented with either 500 nM HB-IGF-1 or 500 nM Xpress-IGF-1. After 48 hours (on day 0), disks were washed 3 times with PBS then incubated in DMEM with no IGF-1. Disks were collected on days 0, 1, 2 and 4. Protein remaining in cartilage extracts was detected by Western blot analysis and ELISA.

Cartilage Biosynthesis Assay

Chondrocyte proteoglycan synthesis was measured by incorporation of [$^{35}$S]sulfate (PerkinElmer, Waltham, Mass., USA) as previously described (Sah, et al., *J. Orthop. Res.* 7:619-636 (1989)). Cartilage disks were equilibrated in serum-free medium for 1 day and incubated in medium containing 100 nM HB-IGF-1, Xpress-IGF-1 or control IGF-1 (Sigma) for 2 days. The disks were then washed 3 times with PBS and changed to IGF-1 free medium. Cultured disks were radiolabeled with 5 μCi/ml [$^{35}$S]sulfate for the final 24 hours of culture. After labeling, each disk was washed 3 times in 1.0 ml of PBS with 0.8 mM proline and 1 mM $Na_2SO_4$ at 4° C. to remove free radiolabel. Disks were digested in 1.0 ml of proteinase K (125 μg/ml in 0.1 M $Na_2SO_4$, 5 mM EDTA and 5 mM cysteine at pH 6.0). Samples were analyzed for DNA content by fluorometric analysis by reaction of 20 μl of digest with 180 μl of Hoechst dye 33258(24). The [$^{35}$S]sulfate content of the digests was then measured in a scintillation counter (Wallac MicroBeta TriLux, PerkinElmer, Waltham, Mass., USA), with corrections for spillover and quenching.

Statistical Analysis

Statistical analyses were performed by Student's t-test with acceptance level $\alpha=0.05$. t-tests were corrected for multiple comparisons using $\alpha=1-(1-\alpha_0)^{1/n}$, where $\alpha_0=0.05$ and n=total number of comparisons. All data were expressed as mean±SE.

Results

Purification of HB-IGF-1

IGF-1 has 3 disulfide bonds and includes 70 amino acids. The IGF-1 fusion proteins both contain poly-histidine tags for protein purification and Xpress tags for protein detection. Molecular weights of HB-IGF-1 and Xpress-IGF-1 are 14,018 Da and 11,548 Da, respectively. HB-IGF-1 has the HB domain on the N-terminus of IGF-1. The HB domain has 21 amino acids and includes 12 positively charged amino acids. Final purification of the new fusion proteins after refolding was performed with RP-HPLC. Identification of the correctly-folded protein was performed as previously described (Milner, et al., *Biochem. J.* 308(Pt 3):865-871 (1995)) and confirmed with bioactivity assays. Coomassie blue staining and Western analysis with an anti-Xpress antibody of the refolded IGF-1 proteins after RP-HPLC, revealed a single band.

HB-IGF-1 Binds to Heparin and Cell Surfaces

We first tested whether HB-IGF-1 binds selectively to heparin. After 2 hours incubation of heparin agarose beads with 300 pmol HB-IGF-1 or Xpress-IGF-1, bound proteins were extracted from beads by boiling. Coomassie blue staining of bound protein with heparin agarose beads showed that HB-IGF-1 binds selectively to heparin compared with Xpress-IGF-1. Next we tested the ability of HB-IGF-1 to bind to cell surfaces, which have heparin sulfate proteoglycans, using 3T3 fibroblast cells and neonatal rat cardiac myocytes. After pretreatment with 0-100 nM of HB-IGF-1 for 2 hours, cells were washed with PBS 3 times. For these experiments, commercial IGF-1 was used as control. HB-IGF-1 bound to 3T3 fibroblast cells when treated with 10 nM and 100 nM concentrations. HB-IGF-1 binding to neonatal cardiac myocytes showed clear selective binding of HB-IGF-1 at 10 nM and 100 nM and a very weak band of IGF-1 at 100 nM. These results are consistent with binding of this HB domain to heparin in the submicromolar range. We also studied the ability of HB-IGF-1 to bind to embryonic stem cells in embryoid bodies, which contain multiple cell types. HB-IGF-1 was readily detected on the surfaces of cells in the embryoid bodies by immunofluorescence for the Xpress epitope tag, indicating that HB-IGF-1 can bind to multiple cell types.

HB-IGF-1 Bioactivity

To determine whether the HB domain interferes with bioactivity, bioassays for IGF-1 receptor phosphorylation and Akt activation were performed. Control IGF-1, HB-IGF-1 and Xpress-IGF-1 all activated the IGF-1 receptor of neonatal cardiac myocytes dose dependently and induced Akt phosphorylation identically. Control IGF-1, HB-IGF-1 and Xpress-IGF-1 all activated Akt within a similar time course. These data demonstrate that addition of the heparin-binding domain does not interfere with the bioactivity of IGF-1.

HB-IGF-1 Transport in Cartilage

Cartilage is a proteoglycan-rich tissue, and chondrocytes respond to IGF-1 with increased extracellular matrix synthesis. Because prolonged local stimulation of IGF-1 signaling could thus be beneficial for cartilage repair, we studied the ability of HB-IGF-1 to bind to cartilage. Identically sized bovine articular cartilage disks were incubated with 500 nM HB-IGF-1 or Xpress-IGF-1 for 1 day, 3 days or 6 days, and there were no differences in the amount of IGF-1 protein that diffused into cartilage over this time period. After pre-incubation with HB-IGF-1 or Xpress-IGF-1 for 48 hours, cartilage disks were washed with PBS at day 0 and similar amounts of IGF-1 were detected. However, on days 1, 2, and 4 after removal of the IGF-1 proteins, only HB-IGF-1 remained in the cartilage, suggesting that HB-IGF-1 bound to the proteoglycan-rich extracellular matrix. In contrast Xpress-IGF-1 was undetectable even 1 day after washing. We also performed this selective binding experiment with cartilage extracts and ELISA measurements. These results confirmed that HB-IGF-1 is selectively retained by cartilage, while Xpress-IGF-1 is rapidly lost.

HB-IGF-1 Increases Chondrocyte Biosynthesis

The selective retention of HB-IGF-1 to cartilage suggests that this fusion protein could deliver a sustained stimulus for chondrocyte biosynthesis. Therefore, we measured chondrocyte biosynthesis of extracellular matrix proteoglycans by incorporation of [$^{35}$S]sulfate. Cartilage disks were incubated with 100 nM HB-IGF-1, control IGF-1 or Xpress-IGF-1 for 2 days and washed 3 times with PBS, followed by culture in medium with no IGF-1. [$^{35}$S]sulfate incorporation was measured for 24 hours beginning on day 0 (before wash-out), day 2 (just after wash-out), day 4, day 6 and day 8. During incubation with the IGF-1 constructs on day 0, control IGF-1, Xpress-IGF-1 and HB-IGF-1 groups all stimulated proteoglycan synthesis as expected. However, after washing, neither control IGF-1 nor Xpress IGF-1 stimulated proteoglycan synthesis at day 4 or beyond. In contrast, HB-IGF-1 led to sustained stimulation of proteoglycan synthesis for 6 days. Proteoglycan synthesis was significantly higher in cartilage incubated with HB-IGF-1 vs. Xpress-IGF-1 on days 2, 4, and 6. These data demonstrate that HB-IGF-1, which is selectively retained in the cartilage, stimulates chondrocyte biosynthesis over a more sustained period.

Discussion

Local delivery of IGF-1 has the potential for improving tissue repair and regeneration while minimizing systemic adverse effects. In this example, we describe a novel IGF-1 protein, HB-IGF-1, that binds to proteoglycan-rich tissue and cell surfaces but has the same bioactivity as IGF-1. Our data indicate that HB-IGF-1 can activate the IGF-1 receptor and Akt and thus that the heparin-binding domain does not interfere with interactions of IGF-1 and its receptor. IGF-1 has four domains: domain (AA1-29), C domain (AA30-41), A domain (AA42-62) and D domain (AA63-70), with the C domain playing the most important role in binding to the IGF-1 receptor. Replacement of the entire C domain causes a 30-fold decrease in affinity for the IGF-1 receptor. Thus, the addition of the heparin-binding domain to the N terminus of IGF-1 was not anticipated to interfere with interactions with the IGF-1 C domain.

Both extracellular matrix and cell surfaces are rich in proteoglycans and can serve as reservoirs for proteoglycan-binding growth factors. A classic example is the fibroblast growth factor-2 (FGF-2) system, where a low affinity, high capacity pool of proteoglycan receptors serves as a reservoir of FGF-2 for its high affinity receptor. Our experiments suggest that HB-IGF-1 could function in some circumstances in a similar manner, since HB-IGF-1 is selectively retained on cell surfaces. IGF-1 can also bind with extracellular matrix via IGF binding proteins (IGFBP); in the circulation, at least 99% of IGF-1 is bound to IGFBPs (IGFBP-1 to -6).

IGF-1 can promote the synthesis of cartilage extracellular matrix and inhibit cartilage degradation (Bonassar, et al., Arch. Biochem. Biophys. 379:57-63 (2000)); however, a practical mode of IGF-1 delivery to cartilage has yet to be developed (Schmidt, et al., Osteoarthritis Cartilage 14:403-412 (2006)). Heparan sulfate proteoglycans are prevalent in the pericellular matrix of cartilage, particularly as chains on perlecan and syndecan-2, and are known to bind other ligands such as FGF-2. Our experiments suggest that HB-IGF-1 protein can bind with matrix and increase local, long-term bioavailability to chondrocytes and thus improve cartilage repair.

In addition to cartilage, HB-IGF-1 has potential for use in other tissues. For example, IGF-1 induces the axon outgrowth of PC12 cells and corticospinal motor neurons, and thus IGF-1 may benefit motor neuron degeneration diseases. In dermal wound healing, IGF-1 is also effective because IGF-1 stimulates collagen synthesis and mitogenicity of fibroblasts and keratinocytes. The ability of HB-IGF-1 to bind to the surfaces of cells may enhance cell therapies and other regenerative strategies.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of treating damaged cartilage tissue in a patient comprising administering to said patient a cell-free composition comprising a polypeptide comprising an insulin-like growth factor-1 (IGF-1) peptide fused to a heparin-binding (HB) peptide from heparin-binding EGF-like growth factor (HB-EGF), wherein said polypeptide binds cartilage tissue and stimulates chondrocyte biosynthesis, and wherein said administering comprises injecting, infusing, implanting, or topically administering said composition at the site of said damaged cartilage tissue.

2. The method of claim 1, wherein said HB peptide comprises the amino acid sequence of SEQ ID NO: 3.

3. The method of claim 1, wherein said IGF-1 comprises the amino acid sequence of SEQ ID NO: 2.

4. The method of claim 1, wherein said IGF-1 comprises the amino acid sequence of SEQ ID NO: 1.

5. The method of claim 1, wherein said composition comprises a pharmaceutically acceptable excipient.

6. The method of claim 1, wherein said polypeptide promotes cartilage regeneration in said cartilage tissue.

7. The method of claim 1, wherein said method comprises injecting, said composition into said patient.

8. The method of claim 1, wherein said method comprises infusing said composition into said patient.

9. The method of claim 1, wherein said method comprises implanting said composition into said patient.

10. The method of claim 1, wherein said IGF-1 comprises amino acids 50-118 of SEQ ID NO: 1.

* * * * *

UNITED STATES PATENT AND TRADEMARK OFFICE
CERTIFICATE OF CORRECTION

PATENT NO. : 9,969,788 B2
APPLICATION NO. : 14/877474
DATED : May 15, 2018
INVENTOR(S) : Richard Lee Page 1 of 1

It is certified that error appears in the above-identified patent and that said Letters Patent is hereby corrected as shown below:

In the Claims

Column 20, Line 46-47, in Claim 7, replace "comprises injecting, said composition into said patient" with --comprises injecting said composition into said patient--.

Signed and Sealed this
Thirty-first Day of July, 2018

Andrei Iancu
*Director of the United States Patent and Trademark Office*